US010004744B2

(12) United States Patent
Cohen et al.

(10) Patent No.: US 10,004,744 B2
(45) Date of Patent: Jun. 26, 2018

(54) THERAPEUTIC APPROACHES FOR TREATING PARKINSON'S DISEASE

(71) Applicant: Pharnext, Issy les Moulineaux (FR)

(72) Inventors: Daniel Cohen, Saint Cloud (FR); Serguei Nabirochkin, Chatenay Malabry (FR); Ilya Chumakov, Vaux le Penil (FR)

(73) Assignee: Pharnext, Issy les Moulineaux (FR)

( * ) Notice: Subject to any disclaimer, the term of this patent is extended or adjusted under 35 U.S.C. 154(b) by 149 days.

(21) Appl. No.: 14/425,926

(22) PCT Filed: Sep. 4, 2013

(86) PCT No.: PCT/EP2013/068312
§ 371 (c)(1),
(2) Date: Mar. 4, 2015

(87) PCT Pub. No.: WO2014/037416
PCT Pub. Date: Mar. 13, 2014

(65) Prior Publication Data
US 2015/0246044 A1    Sep. 3, 2015

Related U.S. Application Data

(60) Provisional application No. 61/696,992, filed on Sep. 5, 2012.

(30) Foreign Application Priority Data

Sep. 5, 2012 (EP) .................... 12306063

(51) Int. Cl.
*A61K 31/137* (2006.01)
*A61K 31/138* (2006.01)
*A61K 31/155* (2006.01)
*A61K 31/185* (2006.01)
*A61K 31/192* (2006.01)
*A61K 31/195* (2006.01)
*A61K 31/197* (2006.01)
*A61K 31/198* (2006.01)
*A61K 31/403* (2006.01)
(Continued)

(52) U.S. Cl.
CPC .......... *A61K 31/519* (2013.01); *A61K 31/137* (2013.01); *A61K 31/138* (2013.01); *A61K 31/155* (2013.01); *A61K 31/185* (2013.01); *A61K 31/192* (2013.01); *A61K 31/195* (2013.01); *A61K 31/197* (2013.01); *A61K 31/198* (2013.01); *A61K 31/216* (2013.01); *A61K 31/403* (2013.01); *A61K 31/4164* (2013.01); *A61K 31/42* (2013.01); *A61K 31/421* (2013.01); *A61K 31/44* (2013.01); *A61K 31/4402* (2013.01); *A61K 31/4422* (2013.01); *A61K 31/445* (2013.01); *A61K 31/506* (2013.01); *A61K 45/06* (2013.01)

(58) Field of Classification Search
CPC .. A61K 31/137; A61K 31/138; A61K 31/155;
A61K 31/185; A61K 31/192; A61K
31/195; A61K 31/197; A61K 31/198;
A61K 31/403; A61K 31/4164; A61K
31/42; A61K 31/421; A61K 31/44; A61K
31/4402; A61K 31/4422; A61K 31/445;
A61K 31/506; A61K 31/519; A61K
31/13; A61K 31/135; A61K 31/165;
A61K 31/24; A61K 31/27; A61K 31/343;
A61K 31/353; A61K 31/4045; A61K
31/416; A61K 31/4178; A61K 31/4184;
A61K 31/428; A61K 31/4458; A61K
31/4525; A61K 31/48; A61K 31/485;
A61K 31/505; A61K 31/55; A61K
31/551; A61K 31/5513; A61K 31/64;
A61K 31/216
See application file for complete search history.

(56) References Cited

U.S. PATENT DOCUMENTS

| 5,677,344 | A | 10/1997 | Greenfield et al. |
| 2009/0069419 | A1* | 3/2009 | Jandeleit ............... C07C 309/15 |
| | | | 514/517 |
| 2009/0076019 | A1 | 3/2009 | Tyers et al. |

FOREIGN PATENT DOCUMENTS

| EP | 2 322 163 | 5/2011 |
| WO | WO 2002/056892 | 7/2002 |

(Continued)

OTHER PUBLICATIONS

Kumar et al. "Neuroprotective effect of carvedilol against aluminum induced toxicity: possible behavioral and biochemical alterations in rats" Pharmacological Reports, 2011, vol. 63, pp. 915-923.*

(Continued)

*Primary Examiner* — Kendra D Carter
(74) *Attorney, Agent, or Firm* — Wolf, Greenfield & Sacks, P.C.

(57) ABSTRACT

The present invention relates to compositions and methods for the treatment of Parkinson's disease and related disorders. More specifically, the present invention relates to novel combinatorial therapies of Parkinson's disease and related disorders targeting the alpha-synuclein aggregation network. In particular, the invention relates to compounds which, alone or in combination(s), can effectively protect neuronal cells from alpha-synuclein aggregates. The invention also relates to methods of producing a drug or a drug combination for treating Parkinson's disease and to methods of treating Parkinson's disease or a related disorder.

12 Claims, No Drawings

(51) Int. Cl.
| | |
|---|---|
| *A61K 31/4164* | (2006.01) |
| *A61K 31/42* | (2006.01) |
| *A61K 31/421* | (2006.01) |
| *A61K 31/519* | (2006.01) |
| *A61K 31/4402* | (2006.01) |
| *A61K 31/4422* | (2006.01) |
| *A61K 31/445* | (2006.01) |
| *A61K 31/506* | (2006.01) |
| *A61K 31/216* | (2006.01) |
| *A61K 31/44* | (2006.01) |
| *A61K 45/06* | (2006.01) |

(56) References Cited

FOREIGN PATENT DOCUMENTS

| WO | WO 2008/089212 | | 7/2008 | |
| --- | --- | --- | --- | --- |
| WO | WO 2009133128 | A1 * | 11/2009 | ........... A61K 31/255 |
| WO | WO 2012/067621 | | 5/2012 | |
| WO | WO 2012/076555 | | 6/2012 | |
| WO | WO 2012/117073 | | 9/2012 | |

OTHER PUBLICATIONS

Jankovic et al. : Current approaches to the treatment of Parkinson's disease, Neuropsychiatric Disease and Treatment, 2008, vol. 4, No. 4, pp. 743-757.*
The Deep-Brain Stimulation for Parkinson's Disease Study Group "Deep-Brain Stimulation of the Subthalamic Nucleus or the Pars Interna of the Globus Pallidus in Parkinson's Disease" N. Engl J. Med., 2001, vol. 345, No. 13, pp. 956-963.*
Dauer et al. Neuron, 2003, vol. 39, pp. 889-909.*
PCT/EP2013/068312, Mar. 7, 2014, International Search Report and Written Opinion.
Follett et al., Pallidal versus subthalamic deep-brain stimulation for Parkinson's disease. N Engl J Med. Jun. 3, 2010;362(22):2077-91.
O'Neil et al., Therapeutic Category and Biological Activity Index: Antiparkinsonian ED. The Merck Index. An Encyclopedia of Chemicals, Drugs, and Biologicals, Whitehouse Station, NJ, USA. Jan. 1, 2006;15. XP002688415.
Suzuki et al., Antioxidant properties of carvedilol: inhibition of lipid peroxidation, protein oxidation and superoxide generation. Neurol Res. Oct. 2003;25(7):749-53.

* cited by examiner

THERAPEUTIC APPROACHES FOR TREATING PARKINSON'S DISEASE

RELATED APPLICATIONS

This application is a national stage filing under 35 U.S.C. § 371 of International Application PCT/EP2013/068312 entitled "NEW THERAPEUTIC APPROACHES FOR TREATING PARKINSON'S DISEASE," filed Sep. 4, 2013, which claims priority to EP Application No. 12306063.4, filed Sep. 5, 2012, and claims the benefit of U.S. provisional application 61/696,992, filed Sep. 5, 2012. Each of the prior applications is incorporated by reference herein in its entirety.

FIELD OF THE INVENTION

The present invention relates to compositions and methods for the treatment of Parkinson's disease and related disorders. More specifically, the present invention relates to novel combinatorial therapies of Parkinson's disease and related disorders.

BACKGROUND OF THE INVENTION

Parkinsonism or Parkinsonian syndromes are a group of progressive, multicentric neurodegenerative disorders whose main features are tremor at rest, rigidity, bradykinesia and postural instability. Parkinson's disease (PD) is the most common form of Parkinsonism and the second most common neurodegenerative disorder after Alzheimer's disease. In industrial countries, the prevalence of PD has been estimated at approximately 0.3% of the general population, the elderly being the most at risk (4% of the population over 80 are estimated to be affected). The mean age of onset is around 60 years, although early onset (as young as 20 year old) can occur [1].

PD is often classified as a movement disorder. Rest tremor is the most common and usually among the earliest symptoms to develop. Bradykinesia also usually appears in the early stages with difficulties performing tasks such as writing or getting dressed. Rigidity occurs and progresses to stiffness and resistance to movement of the whole body, reducing the ability to move. In the late stages, the disease progresses to postural instability, leading to impaired balance and frequent falls. Other motor symptoms such as gait or swallowing disturbances can arise. If not treated, motor symptoms can lead to the patient being bedridden after an average of ten years [2, 3].

In later stages of the disease, PD gives rise to many non-motor symptoms which vary greatly individually. Disability is then greatly worsened by the development of autonomic and neuropsychiatric disturbances. Disorders of speech, cognition, mood, behavior, and/or thought will develop, leading eventually to dementia. Other common symptoms include sensory, sleep and emotional problems. Those disorders decrease the life expectancy of the individual affected and the mortality ratios are around twice those of people without PD [2-4].

PD is an idiopathic disease and its pathophysiology also remains poorly understood [4]. However, at least 5% of PD cases can be attributed to genetic variations. Mutations within genes such as SNCA (alpha-synuclein), PRKN (parkin), LRRK2 (leucine-rich repeat kinase 2), PINK1 (PTEN-induced putative kinase 1), DJ-1 and ATP13A2 and eleven gene loci (PARK1-PARK11) have been associated with familial PD [5]. Apart from genetic factors, many environmental risk factors have been proposed to be involved in the onset of PD but none with undisputed evidence. The most frequently replicated risk factor is exposure to pesticides or herbicides such as Agent Orange. On another hand, smoking and caffeine consumption seem to protect individuals from PD [1].

The pathophysiology of PD is characterized by three features [4]:

(i) A synucleinopathy characterized by the abnormal accumulation of alpha-synuclein protein into inclusions called Lewy bodies in the brain. The distribution of the Lewy bodies throughout the brain varies from one individual to another but is often directly associated with the expression and degree of the clinical symptoms.

(ii) A dopaminergic activity deficiency due to the death of dopamine-generating cells in the substantia nigra, a region of the midbrain. This results in a loss of muscle movement and tone control, leading to the motor symptoms of PD.

(iii) Degeneration of NANC (non-adrenergic, non-cholinergic), serotonergic and cholinergic neurons also occurs in later stages of the disease, leading to the non-motor symptoms of PD.

As no biological tests are available, diagnosis of PD is mainly based on observation of clinical symptoms and exclusion of other disorders with similar clinical features [3]. Postmortem confirmation is required for a definitive diagnosis. Neurological examination by neuroimaging can be useful to detect changes in dopaminergic neurons and to rule out other diseases. Positive therapeutic response to levodopa is another diagnosis criterion. Once the diagnosis made, the progression and severity of the disease is rated using a stages scale such as the Unified Parkinson's Disease Rating Scale.

The most widely used treatment, especially at earlier stages, is the dopamine precursor levodopa (L-DOPA) [6]. The drug brings the lacking neurotransmitter to the dopaminergic neurons, thus decreasing motor symptoms. However, most of the drug is metabolized before to reach the blood brain barrier, causing a variety of side effects, especially dyskinesia [7]. To prevent this phenomenon, L-DOPA is therefore usually given in combination with carbidopa or benserazide (peripheral dopa decarboxylase inhibitors) and often also with catechol-O-methyl transferase inhibitors such as entacapone. These drugs aim at preventing L-DOPA metabolism before to reach the brain, enhancing the activity of the drug [6]. Although less effective at improving motor symptoms, dopamine agonists such as pergolide, cabergoline, apomorphine or lisuride and monoamine oxidase-B inhibitors (involved in the catabolic breakdown of dopamine) such as selegiline or rasagiline are commonly used at early stages of the disease. Although less effective, they may be useful at delaying the use of levodopa and thus the onset of dyskinesia [7].

Other drugs such as anticholinergics and nicotinic acetylcholine receptor may be useful but their efficacy for PD remains to be confirmed [7]. Current research also focuses on neuroprotective treatments, but none of them provided evidence of improved degeneration. They target apoptosis (omigapil, CEP-1347), glutamate receptors, adenosine A2A receptor, calcium channels (isradipine), growth factors (GDNF), alpha-synuclein and inflammation [8]. Ongoing pharmaceutical research has shown a growing interest on gene therapy and neural transplantation [8].

PD remains so far an incurable disease and no effective disease-modifying treatment has been discovered yet. Therefore, current treatments aim at relieving symptoms and alleviate the slow progression of the disease.

SUMMARY OF INVENTION

The present invention relates to compositions and methods for the treatment of Parkinson's disease and related disorders.

More particularly, an object of the invention relates to a composition for use in the treatment of Parkinson's disease or a related disorder, comprising at least two compounds selected from the group consisting of carbetapentane, rilmenidine, acamprosate, baclofen, buphenine, carvedilol, cimetidine, cinacalcet, ciprofibrate, dexbrompheniramine, ifenprodil, metformin, mexiletine, moxonidine, nitrendipine, torasemide and triamterene, or a salt, prodrug, derivative of any chemical purity, or sustained release formulation thereof, for simultaneous, separate or sequential administration.

In a preferred embodiment, the composition comprises
  a) at least one compound selected from baclofen and mexiletine; and
  b) at least one compound selected from acamprosate, cinacalcet and torasemide.

The compositions of the invention may further comprise additional active agents, preferably selected from amiloride, amlexanox, bezafibrate, carbamazepine, gabapentin, ibudilast, leflunomide, losartan, methimazole, naproxen, nicardipine, nicergoline, perhexiline, pyrimethamine, sulodexide and telmisartan, or salts or prodrugs or derivatives of any purity or sustained release formulations thereof.

Most preferred compositions of the invention comprise at least one of the following combinations of compounds:
  carbetapentane and rilmenidine,
  baclofen and acamprosate,
  mexiletine and cinacalcet,
  torasemide and baclofen,
  carbetapentane and carvedilol,
  cimetidine and rilmenidine,
  rilmenidine and metformin,
  rilmenidine and nitrendipine,
  metformin and nitrendipine,
  baclofen and acamprosate and carbetapentane,
  baclofen and acamprosate and rilmenidine,
  baclofen and acamprosate and nitrendipine,
  baclofen and acamprosate and leflunomide,
  carbetapentane and rilmenidine and levodopa,
  cimetidine and rilmenidine and levodopa,
  rilmenidine and metformin and levodopa,
  rilmenidine and nitrendipine and levodopa,
  metformin and nitrendipine and levodopa,
  mexiletine and cinacalcet and levodopa,
  torasemide and baclofen and levodopa,
  baclofen and acamprosate and leflunomide,
  baclofen and acamprosate and leflunomide and levodopa,
  baclofen and acamprosate and levodopa, or
  baclofen and acamprosate and rilmenidine and levodopa.

A further object of the invention resides in a method of treating Parkinson's disease or a related disorder in a mammalian subject in need thereof, the method comprising simultaneously, separately or sequentially administering to a subject an effective amount of a composition as defined above.

The invention also relates to pharmaceutical compositions per se comprising drug combinations as disclosed in the present application.

The methods and compositions of the invention may be used in any mammalian subject, particularly in human subjects, in need thereof. The invention may be used in a curative treatment, or in a preventive regimen, especially in subjects at risk of PD or a related disorder.

DETAILED DESCRIPTION OF THE INVENTION

It is an object of the present invention to provide new therapeutic approaches for treating Parkinson's disease and related disorders. The invention discloses novel use of drugs, novel drug combinations and methods, which allow an effective correction of such diseases and may be used in any mammalian subject.

PD is a neurodegenerative disorder leading to motor and non-motor manifestations and characterized by extensive degeneration of dopaminergic neurons in the nigrostriatal system. Several biological processes such as oxidative stress, mitochondrial dysfunction and neuroinflammation are involved in the accumulation of aggregated alpha-synuclein which leads to the degeneration of dopaminergic neurons.

The inventors were able to establish a network underlying alpha-synuclein aggregation which is a major functional network affected in Parkinson's disease. The inventors have identified functional modules composed of several target proteins, within the alpha-synuclein aggregation network. Such proteins are functionally relevant to the genesis and control of Parkinson's disease, and represent valuable targets for therapies and particularly combination therapies. Accordingly, the inventors discovered drugs which can effectively modulate the alpha-synuclein aggregation network through interacting with said relevant proteins families.

Hence, the invention relates to the use of particular drugs which, alone but preferentially in combinations, modulate the above pathways and may be used to treat said Parkinson's disease and related disorders.

In a particular embodiment, the present invention more specifically relates to compositions and methods using a drug combination that inhibits the activity of at least two distinct proteins involved in alpha-synuclein aggregation network. Thus, therapeutic approaches of the invention are effective for the protection of neuronal cells particularly for the protection of dopaminergic neurons in the midbrain and more particularly in the substantia nigra.

The motor manifestations of PD are attributable to the degeneration of dopaminergic neurons within the substantia nigra. They include tremor, bradykinesia, rigidity, postural instability, abnormal gait and swallowing disturbances. Non-motor symptoms include autonomic and neuropsychiatric disturbances such as anosmia, or sleep abnormalities.

The invention is particularly suited for treating PD and related disorders. In the context of this invention, the term "related disorder" includes tremor, bradykinesia, rigidity, postural instability, abnormal gait, anosmia, sleep abnormalities.

As used herein, "treatment" includes the therapy, prevention, prophylaxis, retardation or reduction of symptoms provoked by or of the causes of Parkinson's disease. The term treatment includes in particular the control of disease progression and associated motor and non-motor symptoms. The term treatment particularly includes i) a protection against the toxicity caused by alpha-synuclein, or a reduction or retardation of said toxicity, and/or ii) a protection of dopaminergic neurons against the toxicity resulting from oxidative stress, mitochondrial dysfunction or neuroinflammation, or a reduction or retardation of said toxicity, in the treated subjects.

Within the context of this invention, the designation of a specific drug or compound is meant to include not only the specifically named molecule, but also any pharmaceutically acceptable salt, hydrate, derivative, isomer, racemate, conjugate, prodrug or derivative thereof of any chemical purity.

The term "combination or combinatorial treating/therapy" designates a treatment wherein at least two or more drugs are co-administered to a subject to cause a biological effect. In a combined therapy according to this invention, the at least two drugs may be administered together or separately, at the same time or sequentially. Also, the at least two drugs may be administered through different routes and protocols. As a result, although they may be formulated together, the drugs of a combination may also be formulated separately.

The term "prodrug" as used herein refers to any functional derivatives (or precursors) of a compound of the present invention, which, when administered to a biological system, generates said compound as a result of e.g., spontaneous chemical reaction(s), enzyme catalysed chemical reaction(s), and/or metabolic chemical reaction(s). Prodrugs are usually inactive or less active than the resulting drug and can be used, for example, to improve the physicochemical properties of the drug, to target the drug to a specific tissue, to improve the pharmacokinetic and pharmacodynamic properties of the drug and/or to reduce undesirable side effects. Some of the common functional groups that are amenable to prodrug design include, but are not limited to, carboxylic, hydroxyl, amine, phosphate/phosphonate and carbonyl groups. Prodrugs typically produced via the modification of these groups include, but are not limited to, esters, carbonates, carbamates, amides and phosphates. Specific technical guidance for the selection of suitable prodrugs is general common knowledge (29-33). Furthermore, the preparation of prodrugs may be performed by conventional methods known by those skilled in the art. Methods which can be used to synthesize other prodrugs are described in numerous reviews on the subject (9; 14-20). For example, Arbaclofen Placarbil is listed in ChemID plus Advance database (website: chem.sis.nlm.nih.gov/chemidplus/) and Arbaclofen Placarbil is a well-known prodrug of baclofen (21-22). Specific examples of prodrugs of baclofen are given in Hanafi et al, 2011 (26), particularly baclofen esters and baclofen ester carbamates, which are of particular interest for CNS targeting. Hence such prodrugs are particularly suitable for compositions of this invention. baclofen placarbil as mentioned before is also a well-known prodrug and may thus be used instead of baclofen in compositions of the invention. Other prodrugs of baclofen can be found in the following patent applications: WO2010102071, US2009197958, WO2009096985, WO2009061934, WO2008086492, US2009216037, WO2005066122, US2011021571, WO2003077902, WO2010120370.

Useful prodrugs for acamprosate such as pantoic acid ester neopentyl sulfonyl esters, neopentyl sulfonyl esters prodrugs or masked carboxylate neopentyl sulfonyl ester prodrugs of acamprosate are notably listed in WO2009033069, WO2009033061, WO2009033054 WO2009052191, WO2009033079, US 2009/0099253, US 2009/0069419, US 2009/0082464, US 2009/0082440, and US 2009/0076147.

The term "derivative" of a compound includes any molecule that is functionally and/or structurally related to said compound, such as an acid, amide, ester, ether, acetylated variant, hydroxylated variant, or an alkylated (C1-C6) variant of such a compound. The term derivative also includes structurally related compound having lost one or more substituent as listed above. For example, Homotaurine is a deacetylated derivative of acamprosate. Preferred derivatives of a compound are molecules having a substantial degree of similarity to said compound, as determined by known methods. Similar compounds along with their index of similarity to a parent molecule can be found in numerous databases such as PubChem (http://pubchem.ncbi.nlm.nih.gov/search/) or DrugBank (http://www.drugbank.ca/). In a more preferred embodiment, derivatives should have a Tanimoto similarity index greater than 0.4, preferably greater than 0.5, more preferably greater than 0.6, even more preferably greater than 0.7 with a parent drug. The Tanimoto similarity index is widely used to measure the degree of structural similarity between two molecules. Tanimoto similarity index can be computed by software such as the Small Molecule Subgraph Detector (23-24) available online (http://www.ebi.ac.uk/thornton-srv/software/SMSD/). Preferred derivatives should be both structurally and functionally related to a parent compound, i.e., they should also retain at least part of the activity of the parent drug, more preferably they should have a protective activity on dopaminergic neurons and more preferably against alpha-synuclein toxicity.

The term derivatives also include metabolites of a drug, e.g., a molecule which results from the (biochemical) modification(s) or processing of said drug after administration to an organism, usually through specialized enzymatic systems, and which displays or retains a biological activity of the drug. Metabolites have been disclosed as being responsible for much of the therapeutic action of the parent drug. In a specific embodiment, a "metabolite" as used herein designates a modified or processed drug that retains at least part of the activity of the parent drug, preferably that has a protective activity on dopaminergic neurons and more preferably against alpha-synuclein toxicity. For example, teriflunomide is a well-known active metabolite of leflunomide. Hence such metabolite is particularly suitable for compositions of the invention.

The term "salt" refers to a pharmaceutically acceptable and relatively non-toxic, inorganic or organic acid addition salt of a compound of the present invention. Pharmaceutical salt formation consists in pairing an acidic, basic or zwitterionic drug molecule with a counterion to create a salt version of the drug. A wide variety of chemical species can be used in neutralization reaction. Pharmaceutically acceptable salts of the invention thus include those obtained by reacting the main compound, functioning as a base, with an inorganic or organic acid to form a salt, for example, salts of acetic acid, nitric acid, tartric acid, hydrochloric acid, sulfuric acid, phosphoric acid, methane sulfonic acid, camphor sulfonic acid, oxalic acid, maleic acid, succinic acid or citric acid. Pharmaceutically acceptable salts of the invention also include those in which the main compound functions as an acid and is reacted with an appropriate base to form, e.g., sodium, potassium, calcium, magnesium, ammonium, or choline salts. Though most of salts of a given active principle are bioequivalents, some may have, among others, increased solubility or bioavailability properties. Salt selection is now a common standard operation in the process of drug development as taught by H. Stahl and C. G Wermuth in their handbook (25).

In a preferred embodiment, the designation of a compound is meant to designate the compound per se, as well as any pharmaceutically acceptable salt, hydrate, isomer, racemate thereof. For example, dexbrompheniramine is the pharmacologically active dextrorotary isomer of brompheniramine.

In a more preferred embodiment, the designation of a compound is meant to designate the compound as specifically designated per se, as well as any pharmaceutically acceptable salt thereof.

In a particular embodiment, a sustained-release formulation of the compound is used.

As disclosed in the examples, molecules of the invention have a strong, unexpected effect on biological processes involved in Parkinson's disease and represent new therapeutic approaches of the pathology. In particular, compositions of the invention have a strong, unexpected effect on alpha-synuclein expression, accumulation and aggregation and thus represent new therapeutic approaches of PD. Furthermore, drugs and drug combinations of the invention, in vitro, increase the dopaminergic neuron survival or protect their neurite length against oxidative stress and, in vivo, induce a protective effect on motor and non-motor symptoms of PD. Thus, therapeutic approaches of the invention are effective for the protection of neuronal cells particularly for the protection of dopaminergic neurons in the midbrain and more particularly in the substantia nigra.

In this regard, in particular embodiment, the invention relates to a composition for use in the treatment of PD or related disorders comprising at least one compound selected from the group consisting of acamprosate, amiloride, amlexanox, baclofen, bezafibrate, buphenine, carbamazepine, carbetapentane, carvedilol, cimetidine, ciprofibrate, cinacalcet, dexbrompheniramine, gabapentin, ibudilast, ifenprodil, leflunomide, losartan, metformin, methimazole, moxonidine, mexiletine, naproxen, nicardipine, nicergoline, nitrendipine, perhexiline, pyrimethamine, rilmenidine, sulodexide, telmisartan, torasemide and triamterene, or a salt, prodrug, derivative of any chemical purity, or sustained release formulation thereof.

In a preferred embodiment, the invention relates to a composition for use in the treatment of PD or related disorders comprising at least one compound selected from the group consisting of acamprosate, baclofen, buphenine, carbetapentane, carvedilol, cimetidine, ciprofibrate, cinacalcet, dexbrompheniramine, ifenprodil, metformin, moxonidine, mexiletine, nitrendipine, rilmenidine, torasemide and triamterene, or a salt, prodrug, derivative of any chemical purity, or sustained release formulation thereof.

Illustrative CAS number for each of these compounds is provided in Table 1 below:

TABLE 1

| DRUG NAME | CAS NUMBER |
|---|---|
| acamprosate | 77337-76-9; 77337-73-6; 107-35-7; 3687-18-1 |
| amiloride | 2609-46-3; 2016-88-8; 17440-83-4 |
| amlexanox | 68302-57-8 |
| baclofen | 1134-47-0; 66514-99-6; 69308-37-8; 70206-22-3; 63701-56-4; 63701-55-3; 847353-30-4 |
| bezafibrate | 41859-67-0 |
| buphenine | 447-41-6; 849-55-8 |
| carbamazepine | 298-46-4 |
| carbetapentane | 77-23-6; 1406-98-0; 23142-01-0; 1045-21-2 |
| carvedilol | 1196658-85-1; 610309-89-2; 374779-41-6; 72956-09-3 |
| cimetidine | 51481-61-9; 70059-30-2; 104057-02-5 |
| cinacalcet | 226256-56-0; 364782-34-3 |
| ciprofibrate | 52214-84-3 |
| dexbrompheniramine | 132-21-8; 2391-03-9; |
| brompheniramine | 86-22-6; 980-71-2 |
| gabapentin | 60142-96-3; 478296-72-9 |
| ibudilast | 50847-11-5 |

TABLE 1-continued

| DRUG NAME | CAS NUMBER |
|---|---|
| ifenprodil | 23210-56-2; 23210-58-4 |
| leflunomide | 75706-12-6 |
| losartan | 114798-26-4; 124750-99-8 |
| metformin | 1115-70-4; 657-24-9 |
| methimazole | 60-56-0 |
| mexiletine | 31828-71-4; 5370-01-4 |
| moxonidine | 75438-57-2; 75438-58-3 |
| naproxen | 22204-53-1; 26159-34-2 |
| nicardipine | 55985-32-5; 54527-84-3 |
| nicergoline | 27848-84-6 |
| nitrendipine | 39562-70-4 |
| perhexiline | 6621-47-2; 6724-53-4 |
| pyrimethamine | 58-14-0 |
| rilmenidine | 54187-04-1; 85409-38-7 |
| sulodexide | 57821-29-1 |
| telmisartan | 144701-48-4 |
| torasemide | 56211-40-6; 72810-59-4 |
| triamterene | 1226-52-4; 396-01-0 |

Considering the functional network of alpha-synuclein aggregation established by inventors, several proteins are involved in alpha-synuclein aggregation and subsequently in the degeneration of dopaminergic neurons thus combinations of these drugs are particularly advantageous.

In this regard, in a particular embodiment, the present invention more specifically relates to compositions and methods using a drug combination that modulate the activity of at least two distinct proteins involved in alpha-synuclein aggregation network.

Combinatorial therapies of the invention are efficient in correcting alpha-synuclein aggregation molecular pathways. Hence, they lead to an improvement of PD through their action on motor as well as non-motor symptoms of the disease. Therapeutic approaches of the invention provide an efficient neuronal protection, particularly dopaminergic neurons, against, mitochondrial dysfunction, excitotoxicity damages, neuroinflammation or apoptosis. More particularly, they can provide a protection of the substantia nigra neurons against the toxicity of aggregated alpha-synuclein to reduce the rate or extent of dopaminergic cell loss and thereby affect the course of the disease progression.

In this regard, a preferred object of this invention relates to a composition comprising a combination of at least two compounds selected from the group consisting of acamprosate, amiloride, amlexanox, baclofen, bezafibrate, buphenine, carbamazepine, carbetapentane, carvedilol, cimetidine, ciprofibrate, cinacalcet, dexbrompheniramine, gabapentin, ibudilast, ifenprodil, leflunomide, losartan, metformin, methimazole, moxonidine, mexiletine, naproxen, nicardipine, nicergoline, nitrendipine, perhexiline, pyrimethamine, rilmenidine, sulodexide, telmisartan, torasemide and triamterene, or salts or prodrugs or derivatives of any purity or sustained release formulations thereof, for use in the treatment of PD or related disorders.

A more preferred object of this invention relates to a composition comprising a combination of at least two compounds selected from the group consisting of acamprosate, baclofen, buphenine, carbetapentane, carvedilol, cimetidine, ciprofibrate, cinacalcet, dexbrompheniramine, ifenprodil, metformin, moxonidine, mexiletine, nitrendipine, rilmenidine, torasemide and triamterene, or salts or prodrugs or derivatives of any purity or sustained release formulations thereof, for use in the treatment of PD or related disorders.

In an even more preferred object of this invention relates to a composition comprising a combination of at least two compounds selected from the group consisting of acamprosate, baclofen, cinacalcet, mexiletine and torasemide, or salts or prodrugs or derivatives of any purity or sustained release formulations thereof, for use in the treatment of PD or related disorders.

Another object of this invention relates to a composition comprising a combination of at least two compounds selected from the group consisting of acamprosate, amiloride, amlexanox, baclofen, bezafibrate, buphenine, carbamazepine, carbetapentane, carvedilol, cimetidine, ciprofibrate, cinacalcet, dexbrompheniramine, gabapentin, ibudilast, ifenprodil, leflunomide, losartan, metformin, methimazole, moxonidine, mexiletine, naproxen, nicardipine, nicergoline, nitrendipine, perhexiline, pyrimethamine, rilmenidine, sulodexide, telmisartan, torasemide and triamterene, or salts or prodrugs or derivatives of any purity or sustained release formulations thereof, for simultaneous, separate or sequential administration.

More preferably this invention relates to a composition comprising a combination of at least two compounds selected from the group consisting of carbetapentane, rilmenidine, acamprosate, baclofen, buphenine, carvedilol, cimetidine, ciprofibrate, cinacalcet, dexbrompheniramine, ifenprodil, metformin, moxonidine, mexiletine, nitrendipine, torasemide and triamterene, or salts or prodrugs or derivatives of any purity or sustained release formulations thereof, for simultaneous, separate or sequential administration.

This invention relates also to a composition comprising a combination of at least two compounds selected from the group consisting of acamprosate, baclofen, cinacalcet, mexiletine and torasemide, or salts or prodrugs or derivatives of any purity or sustained release formulations thereof, for simultaneous, separate or sequential administration.

The inventors further discovered that combination of at least one drug combination selected from the group consisting of baclofen and acamprosate, mexiletine and cinacalcet, or torasemide and baclofen with drug(s) or drug(s) combination(s) described above can enhance their therapeutic effect and lead to even more efficient compositions for use in the treatment of PD or related disorders.

More preferably, drug compositions of the invention may comprise 1, 2, 3, 4 or 5 distinct drugs, even more preferably 2, 3 or 4 distinct drugs for combinatorial treatment of Parkinson's disease (PD) or a related disorder in a subject in need thereof. In a preferred embodiment, the drugs of the invention are used in combination(s) for combined, separate or sequential administration, in order to provide the most effective effect.

In a most preferred embodiment, compositions of this invention, for use in the treatment of PD or related disorders, comprise at least one of the following drug combinations, for combined, separate or sequential administration:
    carbetapentane and rilmenidine,
    baclofen and acamprosate,
    mexiletine and cinacalcet,
    torasemide and baclofen,
    carbetapentane and carvedilol,
    cimetidine and rilmenidine,
    rilmenidine and metformin,
    rilmenidine and nitrendipine,
    metformin and nitrendipine,
    baclofen and acamprosate and carbetapentane,
    baclofen and acamprosate and rilmenidine,
    baclofen and acamprosate and nitrendipine, or
    baclofen and acamprosate and leflunomide.

The invention also relates to a composition comprising at least one of the following drug combinations, or salts, prodrugs, derivatives or sustained release formulations thereof, the drugs in each of said combinations being for simultaneous, separate or sequential administration:
    baclofen and acamprosate,
    mexiletine and cinacalcet,
    torasemide and baclofen,
    carbetapentane and carvedilol,
    cimetidine and rilmenidine,
    rilmenidine and metformin,
    rilmenidine and nitrendipine,
    metformin and nitrendipine,
    baclofen and acamprosate and rilmenidine,
    baclofen and acamprosate and nitrendipine, or
    baclofen and acamprosate and leflunomide.

A further object of this invention resides in the use of a composition as defined above for the manufacture of a medicament for treating PD or a related disorder.

As indicated previously, in a combination therapy of this invention, the compounds or drugs may be formulated together or separately, and administered together, separately or sequentially.

A further object of the invention is a method of treating PD or a related disorder, the method comprising simultaneously, separately or sequentially administering to a subject in need thereof an effective amount of a composition as disclosed above.

In this regard, a particular object of the invention is a method of treating PD or a related disorder, the method comprising simultaneously, separately or sequentially administering to a subject in need thereof an effective amount of a drug combination as defined above.

In another embodiment, the invention relates to a method of treating PD or a related disorder in a subject in need thereof, comprising administering simultaneously, separately or sequentially to the subject an effective amount of at least one compound selected from the group consisting of acamprosate, amiloride, amlexanox, baclofen, bezafibrate, buphenine, carbamazepine, carbetapentane, carvedilol, cimetidine, ciprofibrate, cinacalcet, dexbrompheniramine, gabapentin, ibudilast, ifenprodil, leflunomide, losartan, metformin, methimazole, moxonidine, mexiletine, naproxen, nicardipine, nicergoline, nitrendipine, perhexiline, pyrimethamine, rilmenidine, sulodexide, telmisartan, torasemide and triamterene.

In a preferred embodiment, the invention relates to a method of treating PD or a related disorder in a subject in need thereof, comprising administering simultaneously, separately or sequentially to the subject an effective amount of a combination of at least two compounds selected from the group consisting of acamprosate, amiloride, amlexanox, baclofen, bezafibrate, buphenine, carbamazepine, carbetapentane, carvedilol, cimetidine, ciprofibrate, cinacalcet, dexbrompheniramine, gabapentin, ibudilast, ifenprodil, leflunomide, losartan, metformin, methimazole, moxonidine, mexiletine, naproxen, nicardipine, nicergoline, nitrendipine, perhexiline, pyrimethamine, rilmenidine, sulodexide, telmisartan, torasemide and triamterene.

In another preferred embodiment, the invention relates to a method of treating PD or a related disorder in a subject in need thereof, comprising administering simultaneously, separately or sequentially to the subject an effective amount of a combination of at least two compounds selected from the group consisting of acamprosate, baclofen, buphenine, carbetapentane, carvedilol, cimetidine, ciprofibrate, cinacalcet, dexbrompheniramine, ifenprodil, metformin, moxonidine, mexiletine, nitrendipine, rilmenidine, torasemide and triamterene.

In an even more preferred embodiment, the invention relates to a method of treating PD or a related disorder in a subject in need thereof, comprising administering simultaneously, separately or sequentially to the subject an effective amount of a combination of at least two compounds selected from the group consisting of acamprosate, baclofen, cinacalcet, mexiletine and torasemide.

The compositions of the invention typically comprise one or several pharmaceutically acceptable carriers or excipients. Also, for use in the present invention, the drugs or compounds are usually mixed with pharmaceutically acceptable excipients or carriers.

In this regard, a further object of this invention is a method of preparing a pharmaceutical composition, the method comprising mixing the above compounds or compound combinations in an appropriate excipient or carrier.

In this regard, a further object of this invention relates to a composition, for use in the treatment of PD or related disorders comprising at least two compounds selected from the group consisting of acamprosate, amiloride, amlexanox, baclofen, bezafibrate, buphenine, carbamazepine, carbetapentane, carvedilol, cimetidine, ciprofibrate, cinacalcet, dexbrompheniramine, gabapentin, ibudilast, ifenprodil, leflunomide, losartan, metformin, methimazole, moxonidine, mexiletine, naproxen, nicardipine, nicergoline, nitrendipine, perhexiline, pyrimethamine, rilmenidine, sulodexide, telmisartan, torasemide and triamterene, or a salt, prodrug, derivative of any chemical purity, or sustained release formulation thereof, in combination with at least one different compound selected from the group consisting of acamprosate, amiloride, amlexanox, baclofen, bezafibrate, buphenine, carbamazepine, carbetapentane, carvedilol, cimetidine, ciprofibrate, cinacalcet, dexbrompheniramine, gabapentin, ibudilast, ifenprodil, leflunomide, losartan, metformin, methimazole, moxonidine, mexiletine, naproxen, nicardipine, nicergoline, nitrendipine, perhexiline, pyrimethamine, rilmenidine, sulodexide, telmisartan, torasemide and triamterene, or a salt, prodrug, derivative of any chemical purity, or sustained release formulation thereof.

In another embodiment, this invention relates to a composition, for use in the treatment of PD or related disorders comprising at least two compounds selected from the group consisting of acamprosate, baclofen, cinacalcet, mexiletine, and torasemide, or a salt, prodrug, derivative of any chemical purity, or sustained release formulation thereof, in combination with at least one different compound selected from the group consisting of acamprosate, amiloride, amlexanox, baclofen, bezafibrate, buphenine, carbamazepine, carbetapentane, carvedilol, cimetidine, ciprofibrate, cinacalcet, dexbrompheniramine, gabapentin, ibudilast, ifenprodil, leflunomide, losartan, metformin, methimazole, moxonidine, mexiletine, naproxen, nicardipine, nicergoline, nitrendipine, perhexiline, pyrimethamine, rilmenidine, sulodexide, telmisartan, torasemide and triamterene, or a salt, prodrug, derivative of any chemical purity, or sustained release formulation thereof.

A preferred object of this invention relates to a composition, for use in the treatment of PD or related disorders comprising baclofen and acamprosate or salts, prodrugs, derivatives or sustained release formulations thereof, in combination with at least one compound selected from the group consisting of amiloride, amlexanox, bezafibrate, buphenine, carbamazepine, carbetapentane, carvedilol, cimetidine, ciprofibrate, cinacalcet, dexbrompheniramine, gabapentin, ibudilast, ifenprodil, leflunomide, losartan, metformin, methimazole, moxonidine, mexiletine, naproxen, nicardipine, nicergoline, nitrendipine, perhexiline, pyrimethamine, rilmenidine, sulodexide, telmisartan, torasemide and triamterene, or a salt, prodrug, derivative of any chemical purity, or sustained release formulation thereof.

A preferred object of this invention relates to a composition, for use in the treatment of PD or related disorders comprising mexiletine and cinacalcet or salts, prodrugs, derivatives or sustained release formulations thereof, in combination with at least one compound selected from the group consisting of acamprosate, amiloride, amlexanox, baclofen, bezafibrate, buphenine, carbamazepine, carbetapentane, carvedilol, cimetidine, ciprofibrate, dexbrompheniramine, gabapentin, ibudilast, ifenprodil, leflunomide, losartan, metformin, methimazole, moxonidine, naproxen, nicardipine, nicergoline, nitrendipine, perhexiline, pyrimethamine, rilmenidine, sulodexide, telmisartan, torasemide and triamterene, or a salt, prodrug, derivative of any chemical purity, or sustained release formulation thereof.

A preferred object of this invention relates to a composition, for use in the treatment of PD or related disorders comprising torasemide and baclofen or salts, prodrugs, derivatives or sustained release formulations thereof, in combination with at least one compound selected from the group consisting of acamprosate, amiloride, amlexanox, bezafibrate, buphenine, carbamazepine, carbetapentane, carvedilol, cimetidine, ciprofibrate, cinacalcet, dexbrompheniramine, gabapentin, ibudilast, ifenprodil, leflunomide, losartan, metformin, methimazole, moxonidine, mexiletine, naproxen, nicardipine, nicergoline, nitrendipine, perhexiline, pyrimethamine, rilmenidine, sulodexide, telmisartan and triamterene, or a salt, prodrug, derivative of any chemical purity, or sustained release formulation thereof.

In another more preferred embodiment, the invention relates to a method of treating PD or a related disorder in a subject in need thereof, comprising administering simultaneously, separately or sequentially to the subject an effective amount of baclofen and acamprosate, in combination with at least one compound selected from the group consisting of amiloride, amlexanox, bezafibrate, buphenine, carbamazepine, carbetapentane, carvedilol, cimetidine, ciprofibrate, cinacalcet, dexbrompheniramine, gabapentin, ibudilast, ifenprodil, leflunomide, losartan, metformin, methimazole, moxonidine, mexiletine, naproxen, nicardipine, nicergoline, nitrendipine, perhexiline, pyrimethamine, rilmenidine, sulodexide, telmisartan, torasemide and triamterene.

In another more preferred embodiment, the invention relates to a method of treating PD or a related disorder in a subject in need thereof, comprising administering simultaneously, separately or sequentially to the subject an effective amount of mexiletine and cinacalcet, in combination with at least one compound selected from the group consisting of acamprosate, amiloride, amlexanox, baclofen, bezafibrate, buphenine, carbamazepine, carbetapentane, carvedilol, cimetidine, ciprofibrate, dexbrompheniramine, gabapentin, ibudilast, ifenprodil, leflunomide, losartan, metformin, methimazole, moxonidine, naproxen, nicardipine, nicergoline, nitrendipine, perhexiline, pyrimethamine, rilmenidine, sulodexide, telmisartan, torasemide and triamterene.

In another more preferred embodiment, the invention relates to a method of treating PD or a related disorder in a subject in need thereof, comprising administering simultaneously, separately or sequentially to the subject an effective amount of torasemide and baclofen, in combination with at least one compound selected from the group consisting of acamprosate, amiloride, amlexanox, bezafibrate, buphenine, carbamazepine, carbetapentane, carvedilol, cimetidine, ciprofibrate, cinacalcet, dexbrompheniramine, gabapentin, ibudilast, ifenprodil, leflunomide, losartan, metformin, methimazole, moxonidine, mexiletine, naproxen, nicardipine, nicergoline, nitrendipine, perhexiline, pyrimethamine, rilmenidine, sulodexide, telmisartan and triamterene.

Although very effective in vitro and in vivo, depending on the subject or specific condition, the above methods, compositions or combination therapies may further be used in conjunction or association or combination with additional drugs or treatments.

Additional therapies used in conjunction with drug(s) or drug(s) combination(s) according to the present invention, may comprise one or more drug(s) that ameliorate symptoms of Parkinson's disease, one or more drug(s) that could be used for palliative treatment of Parkinson's disease or one or more drug(s) currently evaluated in the frame of clinical trials for treating of Parkinson's disease.

Therefore, compositions of the invention can be combined with dopaminergic drugs such as dopamine precursors (preferably levodopa), dopamine receptor agonists (preferably pergolide, cabergoline, lisuride, pramipexole, ropinirole or apomorphine) or inhibitors of dopamine-metabolizing enzymes (preferably selegiline, rasagiline, tolcapone or entacapone).

Compositions of the invention can also be combined with treatment of the non-motor symptoms of PD, preferably Clozapine, Desipramine, Citalopram, Nortriptyline, Paroxetine, Atomoxetine, Venlafaxine, Amantadine, Donepezil, Rivastigmine or Memantine.

In this regard, a further object of this invention relates to a composition, for use in the treatment of PD or related disorders, comprising a composition as defined above, in combination with at least one compound selected from the group consisting of levodopa, pergolide, cabergoline, lisuride, pramipexole, ropinirole, apomorphine, selegiline, rasagiline, tolcapone, entacapone, clozapine, desipramine, citalopram, nortriptyline, paroxetine, atomoxetine, venlafaxine, amantadine, donepezil, rivastigmine and memantine, or salts or prodrugs or derivatives of any purity or sustained release formulations thereof.

In another embodiment, the invention relates to a composition for use in the treatment of PD and related disorders, comprising at least one compound selected from the group consisting of acamprosate, amiloride, amlexanox, baclofen, bezafibrate, buphenine, carbamazepine, carbetapentane, carvedilol, cimetidine, ciprofibrate, cinacalcet, dexbrompheniramine, gabapentin, ibudilast, ifenprodil, leflunomide, losartan, metformin, methimazole, moxonidine, mexiletine, naproxen, nicardipine, nicergoline, nitrendipine, perhexiline, pyrimethamine, rilmenidine, sulodexide, telmisartan, torasemide and triamterene or salt(s), prodrug(s), derivative(s) of any chemical purity, or sustained-release formulation(s) thereof, in combination with at least one compound selected from the group consisting of levodopa, pergolide, cabergoline, lisuride, pramipexole, ropinirole, apomorphine, selegiline, rasagiline, tolcapone, entacapone, clozapine, desipramine, citalopram, nortriptyline, paroxetine, atomoxetine, venlafaxine, amantadine, donepezil, rivastigmine and memantine, or salts or prodrugs or derivatives of any purity or sustained release formulations thereof.

In a preferred embodiment, the invention relates to a composition for use in the treatment of PD and related disorders, comprising at least two compounds selected from the group consisting of acamprosate, amiloride, amlexanox, baclofen, bezafibrate, buphenine, carbamazepine, carbetapentane, carvedilol, cimetidine, ciprofibrate, cinacalcet, dexbrompheniramine, gabapentin, ibudilast, ifenprodil, leflunomide, losartan, metformin, methimazole, moxonidine, mexiletine, naproxen, nicardipine, nicergoline, nitrendipine, perhexiline, pyrimethamine, rilmenidine, sulodexide, telmisartan, torasemide and triamterene or salt(s), prodrug(s), derivative(s) of any chemical purity, or sustained-release formulation(s) thereof, in combination with at least one compound selected from the group consisting of levodopa, pergolide, cabergoline, lisuride, pramipexole, ropinirole, apomorphine, selegiline, rasagiline, tolcapone, entacapone, clozapine, desipramine, citalopram, nortriptyline, paroxetine, atomoxetine, venlafaxine, amantadine, donepezil, rivastigmine and memantine, or salts or prodrugs or derivatives of any purity or sustained release formulations thereof.

In another preferred embodiment, the invention relates to a composition for use in the treatment of PD and related disorders, comprising at least two compounds selected from the group consisting of acamprosate, baclofen, buphenine, carbetapentane, carvedilol, cimetidine, ciprofibrate, cinacalcet, dexbrompheniramine, ifenprodil, metformin, moxonidine, mexiletine, nitrendipine, rilmenidine, torasemide and triamterene, or salt(s), prodrug(s), derivative(s) of any chemical purity, or sustained-release formulation(s) thereof, in combination with at least one compound selected from the group consisting of levodopa, pergolide, cabergoline, lisuride, pramipexole, ropinirole, apomorphine, selegiline, rasagiline, tolcapone, entacapone, clozapine, desipramine, citalopram, nortriptyline, paroxetine, atomoxetine, venlafaxine, amantadine, donepezil, rivastigmine and memantine, or salts or prodrugs or derivatives of any purity or sustained release formulations thereof.

In a more preferred embodiment, the invention relates to a composition for use in the treatment of PD and related disorders, comprising at least two compounds selected from the group consisting of acamprosate, baclofen, cinacalcet, mexiletine and torasemide, or salt(s), prodrug(s), derivative(s) of any chemical purity, or sustained-release formulation(s) thereof, in combination with at least one compound selected from the group consisting of levodopa, pergolide, cabergoline, lisuride, pramipexole, ropinirole, apomorphine, selegiline, rasagiline, tolcapone, entacapone, clozapine, desipramine, citalopram, nortriptyline, paroxetine, atomoxetine, venlafaxine, amantadine, donepezil, rivastigmine and memantine, or salts or prodrugs or derivatives of any purity or sustained release formulations thereof.

In an even more preferred embodiment, compositions of this invention, for use in the treatment of PD or related disorders treatment, comprise at least one of the following drug combinations, for combined, separate or sequential administration:
  carbetapentane and rilmenidine and levodopa,
  cimetidine and rilmenidine and levodopa,
  rilmenidine and metformin and levodopa,
  rilmenidine and nitrendipine and levodopa,
  metformin and nitrendipine and levodopa,
  baclofen and acamprosate and levodopa,
  mexiletine and cinacalcet and levodopa,
  torasemide and baclofen and levodopa,
  baclofen and acamprosate and leflunomide and levodopa,
  baclofen and acamprosate and rilmenidine and levodopa.

The invention also relates to a composition comprising at least one of the following drug combinations, or salts, prodrugs, derivatives or sustained release formulations thereof, the drugs in each of said combinations being for simultaneous, separate or sequential administration:
  carbetapentane and rilmenidine and levodopa,
  cimetidine and rilmenidine and levodopa,
  rilmenidine and metformin and levodopa, rilmenidine and nitrendipine and levodopa,
metformin and nitrendipine and levodopa,
baclofen and acamprosate and levodopa,
mexiletine and cinacalcet and levodopa,
torasemide and baclofen and levodopa,
baclofen and acamprosate and leflunomide and levodopa,
baclofen and acamprosate and rilmenidine and levodopa.

In a particular embodiment, when compositions or combination therapies of the invention comprise dopamine precursor, they can be further combined with at least one compound selected from peripheral dopa decarboxylase inhibitors or catechol-O-methyl transferase inhibitors. More particularly, when compositions or combination therapies of the invention comprise a dopamine precursor, they can be further combined with at least one compound selected from carbidopa, benserazide or entacapone.

In another embodiment, compositions or combination therapies of the invention can be used in conjunction with surgical therapy for Parkinson's disease such as deep brain stimulation. More particularly, surgical therapies are deep brain stimulation of the subthalamic nucleus or of the globus pallidus interna.

In this regard, the invention relates to a composition comprising at least one compound selected from the group consisting of acamprosate, amiloride, amlexanox, baclofen, bezafibrate, buphenine, carbamazepine, carbetapentane, carvedilol, cimetidine, ciprofibrate, cinacalcet, dexbrompheniramine, gabapentin, ibudilast, ifenprodil, leflunomide, losartan, metformin, methimazole, moxonidine, mexiletine, naproxen, nicardipine, nicergoline, nitrendipine, perhexiline, pyrimethamine, rilmenidine, sulodexide, telmisartan, torasemide and triamterene, or salt(s), prodrug(s), derivative(s) of any chemical purity, or sustained-release formulation(s) thereof, for use in combination with deep brain stimulation of the subthalamic nucleus or of the globus pallidus interna, in the treatment of PD and related disorders.

PD motor symptoms can develop lately when the dopaminergic denervation of the striatum and lose of substantia nigra dopaminergic neurons are already widely occurring. Thus, the treatment of PD before motor symptoms appearance and in prevention is essential in order to alter the progression and course of the disease.

In this regard, in a preferred embodiment, the above methods, compositions or combination therapies can be used for the prevention, prophylaxis or retardation of symptoms provoked by or of the causes of Parkinson's disease.

The combination of early detection of non-motor symptoms, most particularly anosmia, with imaging techniques (Single-photon emission computed technology, Positron Emission Tomography) to assess changes in striatal dopamine transporter may be a suitable approach to identify at risk PD patients prior to the appearance of motor symptoms, thus allowing early start of neuroprotective therapy.

Some PD cases can be attributed to mutations within genes such as SNCA (alpha-synuclein), PRKN (parkin), LRRK2 (leucine-rich repeat kinase 2), PINK1 (PTEN-induced putative kinase 1), DJ-1 and ATP13A2 and eleven gene loci (PARK1-PARK11). In this regard, in a particular embodiment, the invention relates to the use of the above methods, compositions or combination therapies for the treatment of PD in a subject having a mutation in at least one of the following genes: SNCA, PRKN, LRRK2, PINK1, DJ-1, ATP13A2 and PARK1 to PARK11.

High concentrations exposure or chronic exposure to metals such as manganese, copper or leads, or chemicals, such as pesticides (e.g. paraquat, rotenone and maneb), are likely to cause PD or related disorders. In this regard, in a particular embodiment, the invention relates to the use of the above methods, compositions or combination therapies in the treatment of PD or related disorders, in a subject exposed, suspected to have been exposed or at risk of be exposed, to chemicals or metals known to be risk factors for developing PD or related disorders.

In a preferred embodiment, the above methods, compositions or combination therapies can be used in a subject who is at risk of developing Parkinson's disease or symptoms associated with Parkinson's disease.

Therapy according to the invention may be provided at home, the doctor's office, a clinic, a hospital's outpatient department, or a hospital, so that the doctor can observe the therapy's effects closely and make any adjustments that are needed.

The duration of the therapy depends on the stage of the disease being treated, age and condition of the patient, and how the patient responds to the treatment. The dosage, frequency and mode of administration of each component of the combination can be controlled independently. For example, one drug may be administered orally while the second drug may be administered intramuscularly. Combination therapy may be given in on-and-off cycles that include rest periods so that the patient's body has a chance to recovery from any as yet unforeseen side-effects. The drugs may also be formulated together such that one administration delivers all drugs.

The administration of each drug of the combination may be by any suitable means that results in a concentration of the drug that, combined with the other component, is able to ameliorate the patient condition or efficiently treat the disease or disorder.

While it is possible for the drugs the combination to be administered as the pure chemical it is preferable to present them as a pharmaceutical composition, also referred to in this context as pharmaceutical formulation. Possible compositions include those suitable for oral, rectal, topical (including transdermal, buccal and sublingual), or parenteral (including subcutaneous, intramuscular, intravenous and intradermal) administration.

More commonly these pharmaceutical formulations are prescribed to the patient in "patient packs" containing a number dosing units or other means for administration of metered unit doses for use during a distinct treatment period in a single package, usually a blister pack.

Patient packs have an advantage over traditional prescriptions, where a pharmacist divides a patient's supply of a pharmaceutical from a bulk supply, in that the patient always has access to the package insert contained in the patient pack, normally missing in traditional prescriptions. The inclusion of a package insert has been shown to improve patient compliance with the physician's instructions. Thus, the invention further includes a pharmaceutical formulation, as herein before described, in combination with packaging material suitable for said formulations. In such a patient pack the intended use of a formulation for the combination treatment can be inferred by instructions, facilities, provisions, adaptations and/or other means to help using the formulation most suitably for the treatment. Such measures make a patient pack specifically suitable for and adapted for use for treatment with the combination of the present invention.

The drug may be contained, in any appropriate amount, in any suitable carrier substance. The drug may be present in an amount of up to 99% by weight of the total weight of the composition. The composition may be provided in a dosage form that is suitable for the oral, parenteral (e.g., intravenously, intramuscularly), rectal, cutaneous, nasal, vaginal, inhalant, skin (patch), or ocular administration route. Thus, the composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, or aerosols.

The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Pharmaceutical compositions according to the invention may be formulated to release the active drug substantially immediately upon administration or at any predetermined time or time period after administration.

The controlled release formulations include (i) formulations that create a substantially constant concentration of the drug within the body over an extended period of time; (ii) formulations that after a predetermined lag time create a substantially constant concentration of the drug within the body over an extended period of time; (iii) formulations that sustain drug action during a predetermined time period by maintaining a relatively, constant, effective drug level in the body with concomitant minimization of undesirable side effects associated with fluctuations in the plasma level of the active drug substance; (iv) formulations that localize drug action by, e.g., spatial placement of a controlled release composition adjacent to or in the diseased tissue or organ; and (v) formulations that target drug action by using carriers or chemical derivatives to deliver the drug to a particular target cell type.

Administration of drugs in the form of a controlled release formulation is especially preferred in cases in which the drug has (i) a narrow therapeutic index (i.e., the difference between the plasma concentration leading to harmful side effects or toxic reactions and the plasma concentration leading to a therapeutic effect is small; in general, the therapeutic index, TI, is defined as the ratio of median lethal dose (LD50) to median effective dose (ED50)); (ii) a narrow absorption window in the gastro-intestinal tract; or (iii) a very short biological half-life so that frequent dosing during a day is required in order to sustain the plasma level at a therapeutic level.

Any of a number of strategies can be pursued in order to obtain controlled release in which the rate of release outweighs the rate of metabolism of the drug in question. Controlled release may be obtained by appropriate selection of various formulation parameters and ingredients, including, e.g., various types of controlled release compositions and coatings. Thus, the drug is formulated with appropriate excipients into a pharmaceutical composition that, upon administration, releases the drug in a controlled manner (single or multiple unit tablet or capsule compositions, oil solutions, suspensions, emulsions, microcapsules, microspheres, nanoparticles, patches, and liposomes).

Solid Dosage Forms for Oral Use

Formulations for oral use include tablets containing the composition of the invention in a mixture with non-toxic pharmaceutically acceptable excipients. These excipients may be, for example, inert diluents or fillers (e.g., sucrose, microcrystalline cellulose, starches including potato starch, calcium carbonate, sodium chloride, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., acacia, alginic acid, sodium alginate, gelatin, starch, pregelatinized starch, microcrystalline cellulose, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., stearic acid, silicas, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug substance in a predetermined pattern (e.g., in order to achieve a controlled release formulation) or it may be adapted not to release the active drug substance until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). A time delay material such as, e.g., glyceryl monostearate or glyceryl distearate may be employed.

The solid tablet compositions may include a coating adapted to protect the composition from unwanted chemical changes, (e.g., chemical degradation prior to the release of the active drug substance). The coating may be applied on the solid dosage form in a similar manner as that described in Encyclopedia of Pharmaceutical Technology.

Drugs may be mixed together in the tablet, or may be partitioned. For example, a first drug is contained on the inside of the tablet, and a second drug is on the outside, such that a substantial portion of the second drug is released prior to the release of the first drug.

Formulations for oral use may also be presented as chewable tablets, or as hard gelatin capsules wherein the active ingredient is mixed with an inert solid diluent (e.g., potato starch, microcrystalline cellulose, calcium carbonate, calcium phosphate or kaolin), or as soft gelatin capsules wherein the active ingredient is mixed with water or an oil medium, for example, liquid paraffin, or olive oil. Powders and granulates may be prepared using the ingredients mentioned above under tablets and capsules in a conventional manner.

Controlled release compositions for oral use may, e.g., be constructed to release the active drug by controlling the dissolution and/or the diffusion of the active drug substance.

Dissolution or diffusion controlled release can be achieved by appropriate coating of a tablet, capsule, pellet, or granulate formulation of drugs, or by incorporating the drug into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated metylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

A controlled release composition containing one or more of the drugs of the claimed combinations may also be in the form of a buoyant tablet or capsule (i.e., a tablet or capsule that, upon oral administration, floats on top of the gastric content for a certain period of time). A buoyant tablet formulation of the drug(s) can be prepared by granulating a mixture of the drug(s) with excipients and 20-75% w/w of hydrocolloids, such as hydroxyethylcellulose, hydroxypropylcellulose, or hydroxypropylmethylcellulose. The obtained granules can then be compressed into tablets. On contact with the gastric juice, the tablet forms a substantially water-impermeable gel barrier around its surface. This gel barrier takes part in maintaining a density of less than one, thereby allowing the tablet to remain buoyant in the gastric juice.

Liquids for Oral Administration

Powders, dispersible powders, or granules suitable for preparation of an aqueous suspension by addition of water are convenient dosage forms for oral administration. Formulation as a suspension provides the active ingredient in a mixture with a dispersing or wetting agent, suspending agent, and one or more preservatives. Suitable suspending agents are, for example, sodium carboxymethylcellulose, methylcellulose, sodium alginate, and the like.

Parenteral Compositions

The pharmaceutical composition may also be administered parenterally by injection, infusion or implantation (intravenous, intramuscular, subcutaneous, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation.

Compositions for parenteral use may be provided in unit dosage forms (e.g., in single-dose ampoules), or in vials containing several doses and in which a suitable preservative may be added (see below). The composition may be in form of a solution, a suspension, an emulsion, an infusion device, or a delivery device for implantation or it may be presented as a dry powder to be reconstituted with water or another suitable vehicle before use. Apart from the active drug(s), the composition may include suitable parenterally acceptable carriers and/or excipients. The active drug(s) may be incorporated into microspheres, microcapsules, nanoparticles, liposomes, or the like for controlled release. The composition may include suspending, solubilizing, stabilizing, pH-adjusting agents, and/or dispersing agents.

The pharmaceutical compositions according to the invention may be in the form suitable for sterile injection. To prepare such a composition, the suitable active drug(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution. The aqueous formulation may also contain one or more preservatives (e.g., methyl, ethyl or n-propyl p-hydroxybenzoate). In cases where one of the drugs is only sparingly or slightly soluble in water, a dissolution enhancing or solubilizing agent can be added, or the solvent may include 10-60% w/w of propylene glycol or the like.

Controlled release parenteral compositions may be in form of aqueous suspensions, microspheres, microcapsules, magnetic microspheres, oil solutions, oil suspensions, or emulsions. Alternatively, the active drug(s) may be incorporated in biocompatible carriers, liposomes, nanoparticles, implants, or infusion devices. Materials for use in the preparation of microspheres and/or microcapsules are, e.g., biodegradable/bioerodible polymers such as polygalactin, poly-(isobutyl cyanoacrylate), poly(2-hydroxyethyl-L-glutamnine). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(glycolic acid) or poly(ortho esters)).

Alternative Routes

Although less preferred and less convenient, other administration routes, and therefore other formulations, may be contemplated. In this regard, for rectal application, suitable dosage forms for a composition include suppositories (emulsion or suspension type), and rectal gelatin capsules (solutions or suspensions). In a typical suppository formulation, the active drug(s) are combined with an appropriate pharmaceutically acceptable suppository base such as cocoa butter, esterified fatty acids, glycerinated gelatin, and various water-soluble or dispersible bases like polyethylene glycols. Various additives, enhancers, or surfactants may be incorporated.

The pharmaceutical compositions may also be administered topically on the skin for percutaneous absorption in dosage forms or formulations containing conventionally non-toxic pharmaceutical acceptable carriers and excipients including microspheres and liposomes. The formulations include creams, ointments, lotions, liniments, gels, hydrogels, solutions, suspensions, sticks, sprays, pastes, plasters, and other kinds of transdermal drug delivery systems. The pharmaceutically acceptable carriers or excipients may include emulsifying agents, antioxidants, buffering agents, preservatives, humectants, penetration enhancers, chelating agents, gel-forming agents, ointment bases, perfumes, and skin protective agents.

The preservatives, humectants, penetration enhancers may be parabens, such as methyl or propyl p-hydroxybenzoate, and benzalkonium chloride, glycerin, propylene glycol, urea, etc.

The pharmaceutical compositions described above for topical administration on the skin may also be used in connection with topical administration onto or close to the part of the body that is to be treated. The compositions may be adapted for direct application or for application by means of special drug delivery devices such as dressings or alternatively plasters, pads, sponges, strips, or other forms of suitable flexible material.

Dosages and Duration of the Treatment

It will be appreciated that the drugs of the combination may be administered concomitantly, either in the same or different pharmaceutical formulation or sequentially. If there is sequential administration, the delay in administering the second (or additional) active ingredient should not be such as to lose the benefit of the efficacious effect of the combination of the active ingredients. A minimum requirement for a combination according to this description is that the combination should be intended for combined use with the benefit of the efficacious effect of the combination of the active ingredients. The intended use of a combination can be inferred by facilities, provisions, adaptations and/or other means to help using the combination according to the invention.

Therapeutically effective amounts of the drugs in a combination of this invention include, e.g., amounts that are effective for reducing Parkinson's disease symptoms, halting or slowing the progression of the disease once it has become clinically manifest, or prevention or reduction of the risk of developing the disease.

Although the active drugs of the present invention may be administered in divided doses, for example two or three times daily, a single daily dose of each drug in the combination is preferred, with a single daily dose of all drugs in a single pharmaceutical composition (unit dosage form) being most preferred.

Administration can be one to several times daily for several days to several years, and may even be for the life of the patient. Chronic or at least periodically repeated long-term administration is indicated in most cases.

The term "unit dosage form" refers to physically discrete units (such as capsules, tablets, or loaded syringe cylinders) suitable as unitary dosages for human subjects, each unit containing a predetermined quantity of active material or materials calculated to produce the desired therapeutic effect, in association with the required pharmaceutical carrier.

The amount of each drug in a preferred unit dosage composition depends upon several factors including the administration method, the body weight and the age of the patient, the stage of the disease, the risk of potential side effects considering the general health status of the person to be treated. Additionally, pharmacogenomic (the effect of genotype on the pharmacokinetic, pharmacodynamic or efficacy profile of a therapeutic) information about a particular patient may affect the dosage used.

Except when responding to especially impairing cases, where higher dosages may be required, the preferred dosage of each drug in the combination will usually lie within the range of doses not above the dosage usually prescribed for long-term maintenance treatment or proven to be safe in phase 3 clinical studies.

One remarkable advantage of the invention is that each compound may be used at low doses in a combination therapy, while producing, in combination, a substantial clinical benefit to the patient. The combination therapy may indeed be effective at doses where the compounds have individually low or no effect. Accordingly, a particular advantage of the invention lies in the ability to use sub-optimal doses of each compound, i.e., doses which are lower than therapeutic doses usually prescribed, preferably ½ of therapeutic doses, more preferably ⅓, ¼, ⅕, or even more preferably ⅒ of therapeutic doses. In particular examples, doses as low as 1/20, 1/30, 1/50, 1/100, or even lower, of therapeutic doses are used.

At such sub-therapeutic dosages, the compounds would exhibit no side effect, while the combination(s) according to the invention are fully effective in treating Parkinson's disease.

A preferred dosage corresponds to amounts from 1% up to 50% of those usually prescribed for long-term maintenance treatment.

The most preferred dosage may correspond to amounts from 1% up to 10% of those usually prescribed for long-term maintenance treatment.

Specific examples of dosages of drugs (Quantity equivalent to active molecule) for use in the invention are provided below:

acamprosate orally from about 1 mg to 500 mg per day,
amiloride orally from about 25 µg to 2 mg per day,
amlexanox orally from about 0.75 mg to 15 mg per day,
baclofen orally from about 0.01 mg to 150 mg per day,
bezafibrate orally from about 2 mg to 60 mg per day,
bupherine orally from about 0.12 mg to 4.8 mg per day,
carbamazepine orally from about 0.6 mg to 600 mg per day,
carbetapentane orally from about 0.6 mg to 18 mg per day,
carvedilol orally from about 62.5 µg to 5 mg per day,
cimetidine orally from about 4 mg to 160 mg per day,
cinacalcet orally from about 0.3 mg to 36 mg per day,
ciprofibrate orally from about 1 mg to 10 mg per day,
dexbrompheniramine orally from about 0.06 mg to 1.2 mg per day,
gabapentin orally from about 3 mg to 360 mg per day,
ibudilast orally from about 0.2 mg to 3 mg per day,
ifenprodil orally from about 0.4 mg to 6 mg per day,
leflunomide orally from about 0.1 mg to 10 mg per day,
losartan orally from about 0.125 mg to 10 mg per day,
metformin orally from about 5 mg to 300 mg per day,
methimazole orally from about 0.05 mg to 6 mg per day,
mexiletine orally from about 6 to 120 mg per day,
moxonidine orally from about 2 µg to 60 µg per day,
naproxen orally from about 5 mg to 150 mg per day
nicardipine orally from about 6 mg to 12 mg per day,
nicergoline orally from about 0.6 mg to 6 mg per day,
nitrendipine orally from about 1 mg to 4 mg per day,
perhexiline orally from about 1 mg to 40 mg per day,
pyrimethamine orally from about 0.75 mg to 7.5 mg per day,
rilmenidine orally from about 10 µg to 200 µg per day,
sulodexide orally from about 0.05 mg to 40 mg per day,
telmisartan orally from about 4 mg to 8 mg per day,
torasemide orally from about 0.05 to 4 mg per day,
triamterene orally from about 1.5 mg to 25 mg per day.

It will be understood that the amount of the drug or the drug combination actually administered will be determined by a physician, in the light of the relevant circumstances including the condition or conditions to be treated, the exact composition to be administered, the age, weight, and response of the individual patient, the severity of the patient's symptoms, and the chosen route of administration. Therefore, the above dosage ranges are intended to provide general guidance and support for the teachings herein, but are not intended to limit the scope of the invention.

The following examples are given for purposes of illustration and not by way of limitation.

EXAMPLES

All animal procedures has been conducted in compliance to the existing legislation and regulations (Decree No. 87-848 of 19 Oct. 1987: implemented in April 1988, incorporated Directive 86/609/EC into French law, amended by Decree No. 2001-464 of 29 May 2001 and by Decision of 20 Jun. 2001).

I. Effect on Alpha-Synuclein Accumulation in Mesencephalic Culture

I.1. Primary Cultures of Dopaminergic Neurons

Rat dopaminergic neurons are cultured as described by Widmer et al., 2000 (29). Briefly, rat fetuses staged at embryonic day (15 days gestation) are removed from cervical dislocation killed female rats. Ventral mesencephalic areas are dissected in cold Dulbecco's modified Eagle medium (DMEM; GIBCO), and cell suspensions are prepared according to published procedures. In brief, tissue pieces are washed two times in DMEM and then mechanically dissociated in 2 ml culture medium by gently pipetting through a 1-ml sterile pipette. Immediately after this trituration approximately 10 ml of medium is added and the undispersed tissue pieces are allowed to settle. Most of the supernatant, which contained the individual cells, is then transferred to a second tube. About 1.5 ml of medium is left in the tube for a second trituration. The cells are spun down and resuspended in 2 ml of DMEM. The cells are seeded at a density of 35000 cells/well in 96 well-plates (wells are pre-coated with poly-L-lysine).

The neurons are grown in culture medium containing 55% DMEM, 32.5% Hanks' balanced salt solution, 1.5% glucose, 10% fetal calf serum, and 1% 0.01 M Hepes. Antibiotics are present for the first 4 days. Cells are incubated at 37° C. in a 95% air/5% CO2-humidified atmosphere. The medium is changed 24 h after plating and, subsequently, every other day.

I.2. Intoxication with 6OHDA and Double Staining

Briefly, on day 6 of culture, the medium is removed and fresh medium with or without 6OHDA (20 µM). 6OHDA (Oxidopamine or 6-hydroxydopamine) is a neurotoxin which selectively kill dopaminergic and noradrenergic neurons.

Test compounds are added at the same time of 6OHDA and let for 48 h.

After 48 hours of intoxication, cells are fixed by a solution of paraformaldhyde 4% for 30 min. After a wash with PBS, the cultures are incubated in a blocking buffer (5% normal goat serum, 0.05% Triton X-100 in PBS) for 30 min. Then the cultures were incubated overnight with mouse anti-α-synuclein antibody diluted in blocking buffer. Following the wash, the cultures are incubated with biotinylated goat anti-mouse antibody for 2 h followed by incubation with Streptavidin Texas-Red for 1 h. For double fluorescent immunostaining, the cultures are further incubated with rabbit anti-tyrosine hydroxylase (TH) antibody overnight, followed by FITC-conjugated goat anti-rabbit antibody for 1 h.

I.3. Results

In vitro assays are carried out with several drugs and combinations of drugs. Drugs and drug combinations of the invention induce a reduction of alpha-synuclein accumulation in the cells induced by 6 OHDA when compared to control conditions.

|  | Reduction of alpha-synuclein accumulation in cells |
|---|---|
| Non treated | − |
| acamprosate | + |
| baclofen | + |
| buphenine | + |
| carbetapentane | + |
| carvedilol | + |
| cimetidine | + |
| cinacalcet | + |
| ciprofibrate | + |
| dexbrompheniramine | + |
| ifenprodil | + |
| leflunomide | + |
| metformin | + |
| mexiletine | + |
| moxonidine | + |
| nitrendipine | + |
| rilmenidine | + |

-continued

|  | Reduction of alpha-synuclein accumulation in cells |
|---|---|
| torasemide | + |
| triamterene | + |

II. Effect on Dopaminergic Neuron Survival and Neurite Length

II.1. Primary Cultures of Dopaminergic Neurons

Dopaminergic neurons are cultivated as previously described (I.1).

II.2. Dopaminergic Neuron Immunostaining Methods and Analysis

Briefly, on day 5 of culture, the medium is removed and replaced by fresh medium supplemented with or without 6OHDA at 60 µM.

Test compounds are added at the same time of 6OHDA and let for 48 h.

After 48 hours of intoxication, cells are fixed by a solution of paraformaldhyde 4% for 30 min at room temperature.

Fixed mesencephalic cells on cover slips are washed in PBS before immunostaining, and they are pre-treated with 1% hydrogen peroxide for 15 min to remove endogenous peroxidase activity. Then, they are incubated with rabbit anti-tyrosine hydroxylase (TH) antibody (1:2000 dilution) overnight at 25° C. in the presence of 0.3% Triton X-100 and normal goat serum. They are the incubated with a biotinylated anti-rabbit IgG (1:200 dilution) for 90 min, and with ABC (Avidin-Biotin-Peroxidase Complex) (1:100 dilution) for 1 h at room temperature. Peroxidase activity is visualized by incubating sections with DAB (3,3'-Diaminobenzidine) in 0.05 M tris-buffered saline (pH 7.6). After several rinses with PBS, samples are mounted on gelatin-coated slices, dehydrated, and coverslipped in histomount medium. Quantification of viable primary mesencephalic dopaminergic cells is performed by counting the TH-immunoreactive cell number in each cover slip. Data are expressed in percentage of control condition.

II.3. Results

In vitro assays are carried out with several drugs and combinations of drugs. Drugs and drug combinations of the invention induce an increase of neuronal survival and a protection of neurites length in mesencephalic culture treated by 6OHDA when compared to control conditions. Combinations listed in the following table have a particular protective effect.

|  | Increase of neuronal survival |
|---|---|
| carbetapentane and rilmenidine | + |
| baclofen and acamprosate | + |
| mexiletine and cinacalcet | + |
| torasemide and baclofen | + |
| carbetapentane and carvedilol | + |
| cimetidine and rilmenidine | + |
| rilmenidine and metformin | + |
| rilmenidine and nitrendipine | + |
| metformin and nitrendipine | + |

III. Effect on Dopaminergic Loss In Vivo and Motor Symptoms

III.1. Animals and Surgical Procedure

Experiments are performed as described by Decressac et al., 2012 (27). Briefly adult female rats, 225-250 g at the time of surgery, are housed two to three per cage with ad libitum access to food and water during a 12 h light/dark cycle.

All surgical procedures are performed under general anaesthesia using a 20:1 mixture of fentanylcitrate (Fentanyl) and medetomidin hypochloride (Dormitor) injected i.p. Rats are placed in a stereotaxic frame and 6-OHDA is injected using a 10 µl Hamilton syringe fitted with a glass capillary (outer diameter of 250 µm).

Partial lesion of the nigro-striatal pathway is obtained by injection of 2×7 µg of 6-OHDA in the striatum at the following coordinates: antero-posterior: +1.2 mm, medio-lateral: −2.5 mm, dorso-ventral: −5.0 mm and antero-posterior: +0.2 mm, medio-lateral: −3.8 mm, dorso-ventral: −5.0 mm (7 µg/3 µl per site; 0.2 µl/min).

III.2. Drug(s) Treatment

On day −1, i.e. 24 h before the 6-OHDA injection, drugs, drug combinations or the vehicle solution are administered per os by gavage twice daily (at 8:00 am and 6:00 pm).

Between day 0 and day 18, drugs, drugs combination or the vehicle solution are administered per os by gavage once or twice daily (at 8:00 am and 6:00 pm). Drugs are solubilized in water and freshly prepared just before each gavage administration.

III.3. Behavioural Testing

Assessment of behavioural function is performed 1 week before, and 3 and 8 weeks after injection of 6-OHDA using four different tests. Tests are performed in the following order:

Cylinder test: the rats are tested for forelimb use asymmetry by the cylinder test and for amphetamine-induced rotational behaviour, as previously described (30). For cylinder test, rats are put in a glass cylinder, a total of 20 forepaw touches are counted and the percentage of left paw touches is determined.

Stepping test: the animals are tested for forelimb akinesia using the stepping test as described earlier (28). On the 2 days preceding the test, the animals are handled by the experimenter to familiarise them with the test procedure. The test is performed on three consecutive days by an experimenter unaware of the group identity of the tested rats. Briefly, the rat is held by the experimenter fixing both hind limbs with one hand and the forelimb not to be monitored with the other, while the unrestrained forepaw is touching the table. The number of adjusting steps is counted while the rat is moved sideways along the table surface (90 cm in 5 s), in the forehand direction. This procedure is repeated twice for each forelimb. The mean of data obtained on three testing days constituted the final dependent variable.

Passive avoidance test: the apparatus is a two-compartment (15×20×15 cm high) box with one illuminated with white polyvinylchloride walls and the other darkened with black polyvinylchloride walls and a grid floor. A guillotine door separates each compartment. A 60 W lamp positioned 40 cm above the apparatus lights up the white compartment during the experiment. Scrambled footshocks (0.3 mA for 3 s) could be delivered to the grid floor using a shock generator scrambler (Lafayette Instruments, Lafayette, USA). The guillotine door is initially closed during the training session. Each mouse is placed into the white compartment. After 5 s, the door raises. When the mouse enters the darkened compartment and places all its paws on the grid floor, the door closes and the footshock is delivered for 3 s. The step-through latency, that is, the latency spent to enter the darkened compartment, and the number of vocalizations is recorded. The retention test is carried out 24 h after training. Each mouse is placed again into the white compartment. After 5 s the doors is raised, the step-through latency and the escape latency, i.e. the time spent to return into the white compartment, are recorded up to 300 s.

II.4. Results

In vivo assays are carried out with drugs or combinations of drugs. Drugs and drug combinations of the invention induce an improvement in motor and non-motor symptoms of PD compared to untreated rats.

REFERENCES 1. de Lau, L. M. and M. M. Breteler, Epidemiology of Parkinson's disease. Lancet Neurol, 2006. 5(6): p. 525-35.
2. Samii, A., J. G. Nutt, and B. R. Ransom, Parkinson's disease. Lancet, 2004. 363(9423): p. 1783-93.
3. Savitt, J. M., V. L. Dawson, and T. M. Dawson, Diagnosis and treatment of Parkinson disease: molecules to medicine. J Clin Invest, 2006. 116(7): p. 1744-54.
4. Schapira, A. H. and P. Jenner, Etiology and pathogenesis of Parkinson's disease. Mov Disord, 2011. 26(6): p. 1049-55.
5. Gao, H. M. and J. S. Hong, Gene-environment interactions: key to unraveling the mystery of Parkinson's disease. Prog Neurobiol, 2011. 94(1): p. 1-19.
6. Abbott, A., levodopa: the story so far. Nature, 2010. 466(7310): p. S6-7.
7. Rascol, O., et al., Milestones in Parkinson's disease therapeutics. Mov Disord, 2011. 26(6): p. 1072-82.
8. Obeso, J. A., et al., Missing pieces in the Parkinson's disease puzzle. Nat Med, 2010. 16(6): p. 653-61.
9. Ettmayer, P., Amidon, G. L., Clement, B. & Testa, B. Lessons learned from marketed and investigational prodrugs. J. Med. Chem. 47, 2393-2404 (2004).
10. Beaumont, K., Webster, R., Gardner, I. & Dack, K. Design of ester prodrugs to enhance oral absorption of poorly permeable compounds: challenges to the discovery scientist. Curr. Drug Metab. 4, 461-485 (2003).
11. Heimbach, T. et al. Enzyme-mediated precipitation of parent drugs from their phosphate prodrugs. Int. J. Pharm. 261, 81-92 (2003).
12. Yang, C. Y., Dantzig, A. H. & Pidgeon, C. Intestinal peptide transport systems and oral drug availability. Pharm. Res. 16, 1331-1343 (1999).
13. Steffansen, B. et al. Intestinal solute carriers: an overview of trends and strategies for improving oral drug absorption. Eur. J. Pharm. Sci. 21, 3-16 (2004).
14. Stella, V. et al. Prodrugs: Challenges and Rewards (AAPS, New York, 2007).
15. Wermuth, C G. The Practice of Medicinal Chemistry. (Hardbound, 2003). Part VI, Chap 33: Designing prodrugs and bioprecursors.
16. Pezron, I. et al. Prodrug strategies in nasal drug delivery. Expert Opin. Ther. Pat., Vol. 12, No. 3, 331-340 (2002).
17. Stella, V. J. Prodrugs as therapeutics. Expert Opin. Ther. Pat. 14, 277-280 (2004).
18. Stella, V. J. & Nti-Addae, K. W. Prodrug strategies to overcome poor water solubility. Adv. Drug Deliv. Rev. 59, 677-694 (2007).
39. Higuchi, T.; Stella, V. eds. Prodrugs As Novel Drug Delivery Systems. ACS Symposium Series. American Chemical Society: Washington, D.C. (1975). 31.
20. Roche, E. B. Design of Biopharmaceutical Properties through Prodrugs and Analogs. American Pharmaceutical Association: Washington, D.C. (1977).
21. Lal, R., et al., Arbaclofen placarbil, a novel R-baclofen prodrug: improved absorption, distribution, metabolism, and elimination properties compared with R-baclofen. J Pharmacol Exp Ther, 2009. 330(3): p. 911-21.
22. Feng Xu, Ge Peng, Thu Phan, Usha Dilip, Jian Lu Chen, Tania Chernov-Rogan, Xuexiang Zhang, Kent Grindstaff, Thamil Annamalai, Kerry Koller, Mark A. Gallop, David J. Wustrow, Discovery of a novel potent GABAB receptor agonist; Bioorg Med Chem Lett. 2011 Nov. 1; 21(21): 6582-5.)
23. Andrew R. Leach, Valerie J. Gillet. An Introduction to Chemoinformatics. Springer 2007.
24. S. Asad Rahman, M. Bashton, G. L. Holliday, R. Schrader and J. M. Thornton: Small Molecule Subgraph Detector (SMSD) Toolkit, Journal of Cheminformatics 2009, 1:12 doi: 10.1186/1758-2946-1-12
25. Stahl H., Wermuth C. G. (Eds.) Handbook of Pharmaceutical Salts: Properties, Selection, and Use. Wiley-VCH; 2 edition (Mar. 29, 2011).
26. Hanafi R, Mosad S, Abouzid K, Niess R, Spahn-Langguth H Baclofen ester and carbamate prodrug candidates: a simultaneous chromatographic assay, resolution optimized with DryLab. J Pharm Biomed Anal. 2011 Nov. 1; 56(3):569-76. Epub 2011 Jul. 1.
27. Decressac, M.; Mattsson, B.; Bjorklund, A., Comparison of the behavioural and histological characteristics of the 6-OHDA and alpha-synuclein rat models of Parkinson's disease. Exp Neurol 2012, 235, (1), 306-15.
28. Kirik, D.; Georgievska, B.; Rosenblad, C.; Bjorklund, A., Delayed infusion of GDNF promotes recovery of motor function in the partial lesion model of Parkinson's disease. Eur J Neurosci 2001, 13, (8), 1589-99.
29. Widmer, H. R.; Schaller, B.; Meyer, M.; Seiler, R. W., Glial cell line-derived neurotrophic factor stimulates the morphological differentiation of cultured ventral mesencephalic calbindin- and calretinin-expressing neurons. Exp Neurol 2000, 164, (1), 71-81.
30. Winkler, C.; Kirik, D.; Bjorklund, A.; Dunnett, S. B., Transplantation in the rat model of Parkinson's disease: ectopic versus homotopic graft placement. Prog Brain Res 2000, 127, 233-65.

The invention claimed is:

1. A method of treating Parkinson's disease (PD) or a related disorder in a mammalian subject in need thereof, the method comprising simultaneously, separately or sequentially administering to the subject an effective amount of at least two compounds selected from the group consisting of carbetapentane, rilmenidine, buphenine, carvedilol, cimetidine, ciprofibrate, dexbrompheniramine, ifenprodil, metformin, mexiletine, moxonidine, nitrendipine, and triamterene, or salts, prodrugs, derivatives of any chemical purity, or sustained release formulation thereof, wherein the subject has Parkinson's disease or a related disorder and wherein the related disorder is selected from the group consisting of tremor, bradykinesia, rigidity, postural instability, and abnormal gait.

2. The method of claim 1, wherein
a) one compound of the at least two compounds is mexiletine.

3. The method of claim 1, wherein said at least two compounds comprise:
carbetapentane and rilmenidine,
carbetapentane and carvedilol,
cimetidine and rilmenidine,
rilmenidine and metformin,
rilmenidine and nitrendipine, or
metformin and nitrendipine.

4. The method of claim 1, further comprising administering to the subject an additional compound selected from the group consisting of amiloride, amlexanox, bezafibrate, carbamazepine, gabapentin, ibudilast, leflunomide, losartan, methimazole, naproxen, nicardipine, nicergoline, perhexiline, pyrimethamine, sulodexide and telmisartan, or salts or prodrugs or sustained release formulations thereof.

5. The method of claim 1, further comprising administering to the subject an additional compound selected from the group consisting of levodopa, pergolide, cabergoline, lisuride, pramipexole, ropinirole, apomorphine, selegiline, rasagiline, tolcapone, entacapone, clozapine, desipramine, citalopram, nortriptyline, paroxetine, atomoxetine, venlafaxine, amantadine, donepezil, rivastigmine and memantine, or salts or prodrugs or sustained release formulations thereof.

6. The method of claim 1, wherein said at least two compounds comprise:
carbetapentane and rilmenidine and levodopa,
cimetidine and rilmenidine and levodopa,
rilmenidine and metformin and levodopa,
rilmenidine and nitrendipine and levodopa, or
metformin and nitrendipine and levodopa.

7. The method of claim 1, wherein said at least two compounds are administered repeatedly to the subject.

8. The method of claim 1, wherein the said subject in need thereof is also treated with deep brain stimulation of the subthalamic nucleus or of the globus pallidus interna.

9. The method of claim 1, wherein one of the at least two compounds is carbetapentane and the other compound of the at least two compounds is selected from the group consisting of rilmenidine, buphenine, carvedilol, cimetidine, ciprofibrate, dexbrompheniramine, ifenprodil, metformin, mexiletine, moxonidine, nitrendipine, and triamterene, or salts, prodrugs, or sustained release formulation thereof.

10. The method of claim 1, wherein said at least two compounds are formulated together.

11. The method of claim 1, wherein said at least two compounds are formulated separately.

12. The method of claim 1, wherein said at least two compounds are selected from the group consisting of carbetapentane, carvedilol, cimetidine, metformin, nitrendipine and rilmenidine, or salts, prodrugs, or sustained release formulations thereof.

* * * * *